United States Patent [19]

Brandestini et al.

[11] Patent Number: 4,837,732

[45] Date of Patent: Jun. 6, 1989

[54] METHOD AND APPARATUS FOR THE THREE-DIMENSIONAL REGISTRATION AND DISPLAY OF PREPARED TEETH

[76] Inventors: Marco Brandestini, Gartenstrasse 10, 8702 Zollikon; Werner H. Moermann, Zweiackerstrasse 57, 8053 Zurich, both of Switzerland

[21] Appl. No.: 58,462

[22] Filed: Jun. 5, 1987

[30] Foreign Application Priority Data

Jun. 24, 1986 [CH] Switzerland .................. 02512/86

[51] Int. Cl.$^4$ .................. G01B 11/24; A61C 19/04; A61C 5/10
[52] U.S. Cl. .................. 364/413.28; 356/376; 433/223
[58] Field of Search .................. 356/1, 376; 364/414, 364/559, 413; 433/223, 204

[56] References Cited

U.S. PATENT DOCUMENTS

| | | | |
|---|---|---|---|
| 4,294,544 | 10/1981 | Altschuler et al. | 356/376 |
| 4,324,546 | 4/1982 | Heitlinger et al. | 433/25 |
| 4,349,274 | 9/1982 | Steele | 356/1 |
| 4,410,787 | 10/1983 | Kremers et al. | 219/124.34 |
| 4,470,122 | 9/1984 | Sarr | 364/559 |
| 4,541,722 | 9/1985 | Jenks | 356/376 |
| 4,575,805 | 3/1986 | Moermann et al. | 364/474 |
| 4,663,720 | 5/1987 | Duret et al. | 364/474 |
| 4,674,869 | 6/1987 | Pryor et al. | 356/1 |

FOREIGN PATENT DOCUMENTS 0262144 12/1985 Japan.

OTHER PUBLICATIONS

B. R. Altschuler, "An Introduction to Dental Laser Holography", pp. i, ii, iv–vi, and 1–28, National Technical Information Service, Mar. 1973.

J. M. Young et al, "Laser Holography in Dentistry", Journal of Prosthetic Dentistry, pp. 216–225, Aug. 1977.

E. D. Rekow et al, "Computer-Aided Automatic Production of Dental Restorations", 1986.

*Primary Examiner*—Clark A. Jablon
*Attorney, Agent, or Firm*—Flynn, Thiel, Boutell & Tanis

[57] ABSTRACT

The method provides a means for a dentist to record the shape in situ of teeth prepared for repair. During a search mode, a high resolution grey scale image is presented on a monitor. The scan head is positioned over the prepared cavity, using this visual feedback. A trigger initiates actual 3D data acquisition, which is accomplished in a fraction of a second using an active triangulation principle. The result is stored in congruent memory banks in the form of a 3D profile and a pseudoplastic grey scale image representing the back-scattered contrast. The pseudoplastic contrast image is displayed instantaneously on the monitor. The point to point relationship between the pseudoplastic grey scale image and the 3D profile allows use of the grey scale display as a drawing plane for operator data verification and editing. The contour lines defining the desired restorative implant appear as an overlay to the grey scale image, while the actual positional values of points on the contour lines are stored in and retrieved from the 3D profile. The contrast-derived pseudoplastic image not only provides higher intelligibility for the operator; but data processing algorithms can also make use for each image point of both sets of data, that is the 3D profile and the contrast image.

28 Claims, 5 Drawing Sheets

METHOD AND APPARATUS FOR THE THREE-DIMENSIONAL REGISTRATION AND DISPLAY OF PREPARED TEETH

FIELD OF THE INVENTION

This invention relates to a method and apparatus for effecting non-contact scanning of a prepared cavity in a tooth followed by automated fabrication of a dental inlay for the cavity and, more particularly, to such a method and apparatus utilizing improved techniques for processing the data which is obtained during the scanning and which is to be used to control the automated inlay fabrication.

BACKGROUND OF THE INVENTION

The invention described herein relates generally to the following conventional situation. A dentist prepares a cavity of a decayed tooth to allow its restoration by means of an inlay, on lay or crown. After the preparation has been rendered, an impression of the cavity is taken, and is ordinarily sent to a dental laboratory. Contrary to conventional techniques, the method and apparatus taught herein utilize a more recent technique, which alleviates the dental laboratory and fabricates the desired restorative piece in the dental office. In particular, the prepared cavity is registered by an electro-optic scan head. The data thus obtained can be complemented by operator input, using techniques from the CAD (Computer-Aided-Design) domain, and the final piece is fabricated with the aid of a miniature NC (numerical control) grinding machine.

In the past few years, several variations of the above theme have been proposed. To highlight a few:

The first description of a system capable of registration and reconstruction of a dental preparation appeared in a report by Bruce R. Altschuler in November '71. The subsequent final report ("An Introduction to Dental Laser Holography", AFSC report SAM-TR-73-4) cites the following concept: "A contour hologram of a prepared tooth for a crown might be used to provide the information to a computer necessary for machining a piece of gold into a dental crown". The same investigator has pursued this concept, and we find further reference in "Laser Holography in Dentistry" by John M. Young and Bruce R. Altschuler, J Prostet. Dent. Aug. 77 pp. 216–225. Inlays are mentioned in this article, and it is reported that prototypes of a system employing a Laser holographic stereocomparator are in use at the Brooks USAF base.

A similar method was described a few years later by the French team of Dr. Francois Duret et al (European Published Application No. 040 165). In line with the advanced state of the art in electronic devices and data processing, the authors of this reference have substituted the classical film hologram by direct interferometric detection, proposing an electronic area sensor. The restoration of the tooth to its original shape was assumed to be highly automated, drawing from a knowledge base stored in the form of a tooth feature library.

Another early description of a dental fitting process is contained in U.S. Pat. No. 3,861,044 by William E. Swinson, Jr. This method teaches the recording of the three-dimensional shape of the cavity by conventional camera means. This process does not seem feasible, and no further reference to this work has been found.

An article by E. Dianne Rekow and Arthur G. Erdman ("Computer-aided Automatic Production of Dental Restorations" Proc. 4th meeting Europ. Soc. of Biomechanics, Davos 1986, p 117 ff.) lists the most promising candidates for the 3D acquisition. The authors chose the method of taking a stereo-pair by means of instant photography and analysing the stereo-pair in a central lab facility, which would also produce the desired piece to be sent back to the dental office to be seated in the tooth cavity during a second session.

Yet another scheme has been devised by Dr. Paul Heitlinger (German Offenlegungsschrift No. 29 36 847 Al, "Method and Apparatus for the Fabrication of Dental Prosthetic Work"). This technique uses a cast replica of the preparation which is recorded stereo-optically. The record is then computer-analysed and processed.

Finally, reference is made to the Inventors' own work, namely European Published Application No. 054 785 and corresponding U.S. Pat. No. 4,575,805. The method taught therein records the data by projecting a ruling onto the preparation and using active triangulation for the determination of depth. This procedure has been successfully utilized on a large number of patients Since the state described in the Inventors' above-mentioned patent, considerable improvements have been added to the basic concepts, and are the subject of the present invention.

Experience has shown that while depth registration alone is adequate, it is not satisfactory to generate reconstructions with the degree of accuracy which is desirable under real-life conditions.

Before commencing a detailed description of the improvements, it is helpful to summarize the operation of a system built according to the technology known to (1) The dentist carries out a three-dimensional scanning or registering of a prepared cavity directly in the patient's mouth.

(2) The recorded three-dimensional data can be visually displayed in two fashions, either as a brightness coded profile (where points closer to the observer appear brighter than those further away) or as a perspective view such as is widely used in the art of CAD (Computer-Aided-Design).

(3) Based on this representation of the shape the preparation, a manual or automatic reconstruction takes place to produce data utilized to control a milling machine which fabricates the restorative part. Preferably, the entire setup is located in the dental office, allowing restoration of one or several teeth in a single session.

SUMMARY OF THE INVENTION

The present invention involves certain basic objects with regard to this basic known concept. First, to ensure that the desired three-dimensional record is taken under the optimum viewing angle, thus showing all the critical parts of the preparation, a search mode with a high quality live video image is to be provided. Without this feature, taking a record from the proper angle and under optimum exposure and focus is an undesirable trial-and-error procedure. High quality means not only that full resolution must be guaranteed, but that all artifacts due to the 3D registration scheme (such as a fringe, speckle and/or venetian blind effect) are intolerable and must be eliminated. It should be mentioned that no on-line 3D system exists today, so the best that can be done is to provide the user with a live 2D image and a rapid, quasi-instantaneous 3D acquisition following a trigger release, the essential condition being that the orientation of the scan head must not change between search and acquisition modes.

As the second object, the result of the 3D acquisition must be displayed instantaneously on the same monitor as and in place of the search image, with identical spatial orientation. This allows the dentist to verify the result, make subtle changes and immediately take a new exposure, if required. The presentation of the recorded tooth features must be accomplished in a manner which is highly intelligible, considering the fact that the dentist is not accustomed to the skills used in technical design work.

The live image and the image which is displayed instantaneously after the 3D acquisition are both pseudoplastic representations of the cavity, that is, the shading of the image suggests three-dimensional features to our visual cortex.

The technique of using this pseudoplastic image as a drawing plane, while retrieving the actual three-dimensional information from a congruent data set, is an important feature of the method presented here.

Objects and purposes of the invention, including those set forth above, are met by providing a method for facilitating acquisition of data defining the three-dimensional shape of prepared teeth and their immediate vicinity, including the steps of: providing a search mode which generates live visual feedback to help establish the orientation of a scan head, and thereafter carrying out trigger initiated, undelayed acquisition of corresponding depth (Z-axis) and backscattered contrast data from the scan head in such established orientation and using the combined depth and contrast data for subsequent image processing.

Objects and purposes of the invention are further met by providing an apparatus for the registration and processing of three-dimensional data representing a prepared tooth and its immediate neighborhood by active triangulation, including means for cancelling from such data artifacts generated by the triangulation so as to provide an uncluttered high resolution live image, and means for acquiring and storing three-dimensional data corresponding to an image of the live sequence at a given point in time.

BRIEF DESCRIPTION OF THE DRAWINGS

The inventive method and apparatus will be described in more detail hereinafter with reference to the accompanying drawings, in which:

FIGS. 4a and 4b are associated views, FIG. 4a being a diagrammatic sectional view of a liquid crystal cell which lends itself to the generation of desired ruling patterns and in particular allows complete suppression of the pattern during processing to yield an uncluttered search mode image, and FIG. 4b being a timing diagram of two exemplary drive signals for the cell of FIG. 4a.

DETAILED DESCRIPTION

The subject matter of the present invention includes improvements to the subject matter disclosed in the Inventors' prior U.S. Pat. No. 4,575,805 issued Mar. 11, 1986, the disclosure of which is hereby incorporated herein by reference. The subject matter of the present invention also relates generally to the Inventors' U.S. Pat. No. 4 615 678 issued Oct. 7, 1986, and the Inventors' U.S. Ser. No. 790 294 filed Oct. 22, 1985, the disclosures of which are hereby incorporated herein by reference.

To facilitate a complete understanding of the present invention, a brief discussion is now given of a portion of the disclosure of the inventors' above-mentioned U.S. Pat. No. 4 575 805. The scan head shown in FIG. 2 of the present application is identical to a scan head disclosed in detail in U.S. Pat. No. 4 575 805, is connected to a computer (at 80 in FIG. 5) which has a video display (56 in FIG. 5) and controls a milling machine (81 in FIG. 5), and operates as follows. A ruling 4 has alternating transparent and opaque stripes which extend perpendicular to the plane of FIG. 2. Light from a light source 2 passes through a condensing lens arrangement 3, the ruling 4, a beam splitter 6, an upper opening of an aperture stop plate 7, an image-forming lens arrangement 8, a prism 9 and a field lens 9A onto a tooth 10 along a path 9B. The ruling 4 produces an intensity pattern which is a series of parallel stripes and is projected onto the tooth 10. Light reflected from the tooth passes through the field lens 9A, the prism 9, the image-forming lens arrangement 8 and a lower hole of the aperture stop plate 7, and then the lower portion of the beam splitter 6 directs the light onto a sensor 11. The sensor 11 is a conventional semiconductor device which includes a two-dimensional array of horizontal rows and vertical columns of sensor elements which each correspond to a respective pixel of a video image produced by the sensor 11. If a planar surface oriented perpendicular to the path 9B is held adjacent the scan head, the light stripes of the intensity pattern reflected by the surface will, after passing through the prism 9, lens arrangement 8, aperture stop plate 7 and beam splitter 6, be reflected onto the sensor 11. Assume that the light stripes each impinge substantially directly on a respective row of sensor elements on the sensor 11. If the planar surface is then slowly moved away from the end of the scan head in a direction parallel to the path 9B, the parallax between the projected and reflected light resulting from the spacing between the two holes in the aperture stop plate 7 will cause the reflected stripe pattern to slowly move vertically on the sensor 11, the vertical shift of each individual stripe being a direct measure of depth. In other words, as a given point on the surface moves further away from the scan head, the amount of light reflected from the region of this point which strikes a respective sensor element of the sensor 11 is modulated in a predetermined fashion. Thus, the intensity of light detected by each sensor element is a direct measure of the distance between the scan head and a corresponding point on an object being scanned.

Figure 1:
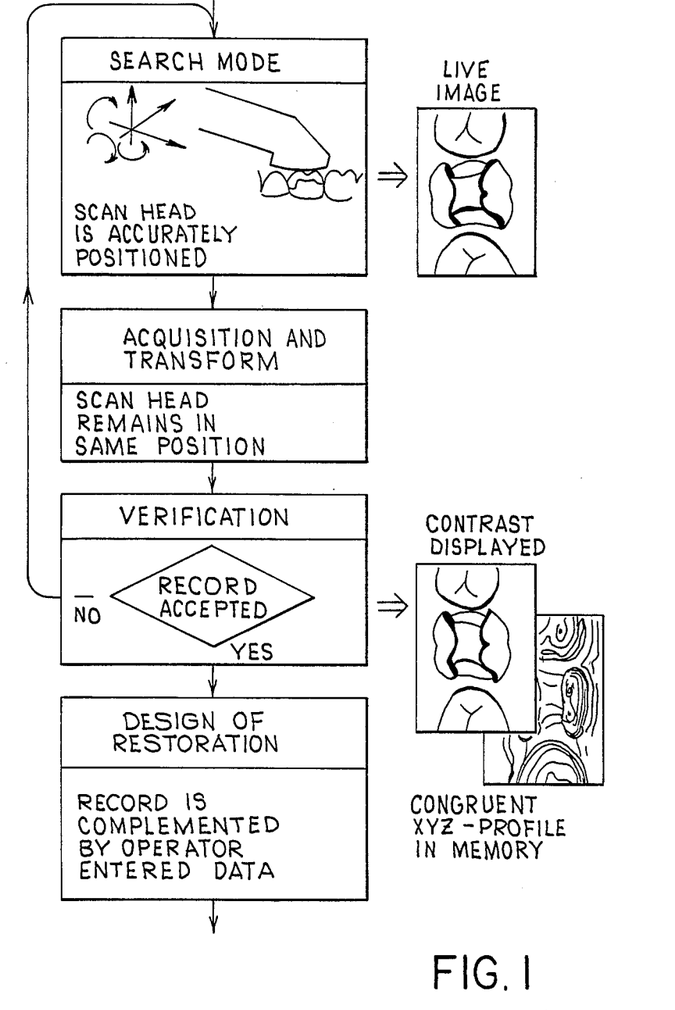
FIG. 1 is a diagrammatic flow chart showing the process of scan head alignment, cavity registration, display and verification, and subsequent action of the operator in the inventive method and apparatus.
Figure 2:
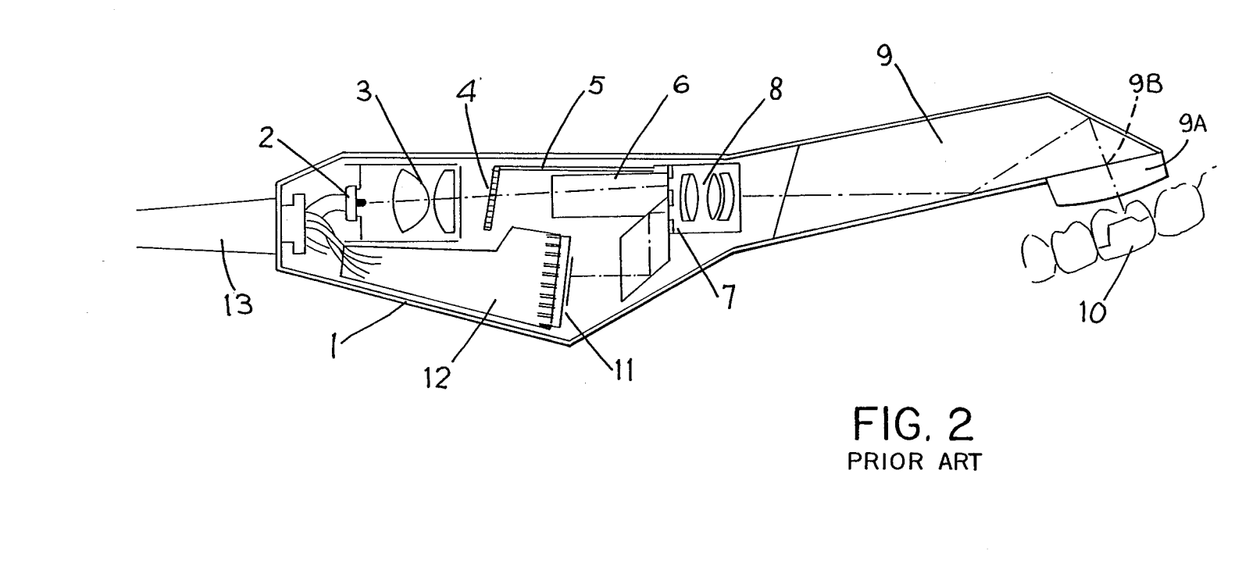
FIG. 2 is a diagrammatic view which shows basic components of a scan head utilized in association with the inventive method and apparatus.

The ruling 4 is supported by a piezoelectric element 5 which, in response to electrical signals, can move the ruling vertically in FIG. 2 to one of four predetermined positions. These positions are spaced from each other by a distance equal to one-fourth of the center-to-center distance between two adjacent opaque lines or rulings on the ruling 4. Since the vertical movement of the ruling effects a vertical movement of the intensity pattern, the respective positions of the ruling will, for convenience, be referred to by the phase shift imparted to the intensity pattern. More specifically, the initial position corresponds to a phase shift of 0°, a vertical shift to the next position by a distance of one-quarter of the spacing between two adjacent lines on the ruling corresponds to a phase shift of 90°, a further shift to the next position by this same distance corresponds to a phase shift of 180°, and a still further shift by this distance to the next-position corresponds to a phase shift of 270°.

According to the teachings of above-mentioned U.S Pat. No. 4,575,805, the scan head can be utilized in tooth 10. With the ruling 4 in its 0° position, the scan head is manually positioned relative to the tooth 10 to be scanned. A computer controlling the scan head will then read and store in its memory a digitized video image based on data from the sensor 19, and will then cause the piezoelectric element 5 to move the ruling 4 to its 90° position. The computer will thereafter read a second digitized video image and store it in its memory, move the ruling to its 180° position, read a third image and store it in memory, move the ruling to its 270° position, and read a fourth image and store it in memory. The time required to read these four images is a small portion of a second. Each of the four images stored in memory will be a 256-by-256 array of 8-bit words, each word corresponding to a respective pixel of the associated video image, the binary number in each word corresponding to the light intensity measured by a respective sensor element of the sensor 11. The computer then processes these four images in the following manner.

The 180° image is subtracted from the 0° image in a pixel-by-pixel manner by reading a binary number from a respective word of the 180° image, subtracting it from the number in the corresponding word of the 0° image, and then saving the result. In a similar manner, the 270° image is subtracted from the 90° image. The result of these two subtractions is thus two differential images in the memory of the computer which will be respectively referred to as the 0°-180° image and the 90°-270° image. Each of these subtractions eliminates any fixed offset present in the intensity measurements at any given sensor element, thereby assuring that each differential is a uniform measure of the difference in intensity of the light reflected from a single location on the object being scanned for two different positions of the ruling which are spaced by a phase shift of 180°. In other words, if one sensor element is slightly more light sensitive than a second sensor element, intensity readings from the first sensor element for a given amount of light will each be slightly greater than intensity readings from the second sensor element for the same amount of light, but when two respective readings of different intensity for each sensor element are subtracted, the differential for the first sensor element will be substantially identical to that for the second.

It should be evident that the 0°-180° image in the memory of the computer effectively leads the 90°-270° image in phase by 90°. Thus, for any given pixel, the two numbers stored in the corresponding locations of the two images can be treated as the real and imaginary parts of a complex vector. The phase angle of this vector is proportional to the distance between the scan head and the associated location on the object being scanned. This phase angle is computed by performing a rectangular-to-polar conversion for each of the pixels in the stored images, each resulting phase angle being stored in the memory to form what will be referred to as a phase angle video image. Each phase angle in the phase angle video image is proportional to the distance parallel to the path 9B between the scan head and the associated location on the object being scanned. Consequently, the phase angle video image is a 3D digital representation of the tooth surface and can be used as a basis for controlling a 3D milling machine so that it machines a dental part such as an inlay which will directly fit the tooth surface. (The values in the phase angle video image are often called "depth" values since they correspond to a physical depth distance into the cavity in the tooth, or "Z-axis" values since the row, column and content of each pixel in the image respectively correspond to coordinates on X, Y and Z axes in a conventional 3D rectangular coordinate system, the Z axis here being parallel to path 9B.)

As mentioned above, the foregoing description summarizes a portion of the disclosure of the inventors'0 U.S. Pat. No. 4,575,805 in order to facilitate an understanding of the present invention. For additional detail, reference should be made directly to such patent. The description which follows is directed to features of the present invention.

During the search mode, the system operates very much like a conventional video camera. The section of th dental arch which is registered by the image sensor 11 (FIG. 2) in the scan head (generally a single tooth and parts of its adjoining neighbors) can be displayed as two interlaced TV fields at a standard 60 Hz rate. (A single standard TV image includes two "fields", one of the fields being every other horizontal line of the image and the other field being the remaining horizontal lines, the two fields thus being "interlaced" to form the image.) Note that the teeth are not only imaged by, but are also illuminated by, the scan head. Since, for the subsequent 3D acquisition, a ruling 4 has been incorporated into the illumination path, care has to be taken during the search mode to eliminate from the resulting data artifacts resulting from the ruling, or in other words remnants of the pattern generated by the ruling. If no special precautions are taken, the striped ruling pattern itself will show in the video image as "venetian blinds", badly cluttering the image. Two methods to cancel this artifact are described below.

The search mode provides the basis for the subsequent 3D record, since it provides the operator with the necessary feedback to position the scan head with respect to the prepared cavity. Ideally, the axis of the scan head, (the dash-dotted line 9B in FIG. 2), should be aligned with the axis along which the inlay is to be inserted. This condition, formulated in other terms, requires that all of the steep walls of the preparation be clearly visible in the image. The scan head is equipped with a telecentric fixed-focus system, and therefore the distance to the prepared cavity must be established in a way to yield a sharp image. Exposure, that is the amount of light projected onto the tooth, must be set to fully exploit the dynamic range of the sensor 11. All of the above parameters are optimized while manually positioning the scan head in the patient's mouth, without any inconvenient and encumbering supports. To facilitate scan head alignment, an electronically generated reticle can be superimposed on the live image as a sighting device.

In the preferred embodiment the search mode is activated while a foot switch is depressed. Release of the switch triggers immediate 3D data acquisition. In the process of 3D acquisition, the ruling 4 is projected onto the preparation in the four different phases discussed above. The resulting patterns are acquired at 33 msec intervals ($4 \times 33 = 133$ msec) and, as described below, stored as two quadrature patterns in memory banks A and B which are respectively shown in FIG. 5 at 54 and 55. The data is then transformed in a manner described below, which takes approximately another 150 msec. As a result of the transformation, the memory banks contain new data, one bank containing a 3D depth profile, as described in above-mentioned U.S. Pat. No. 4,575,805, and the other bank containing as an invaluable addition, the contrast of the backscattered pattern for each picture element (pixel).

Figure 5:
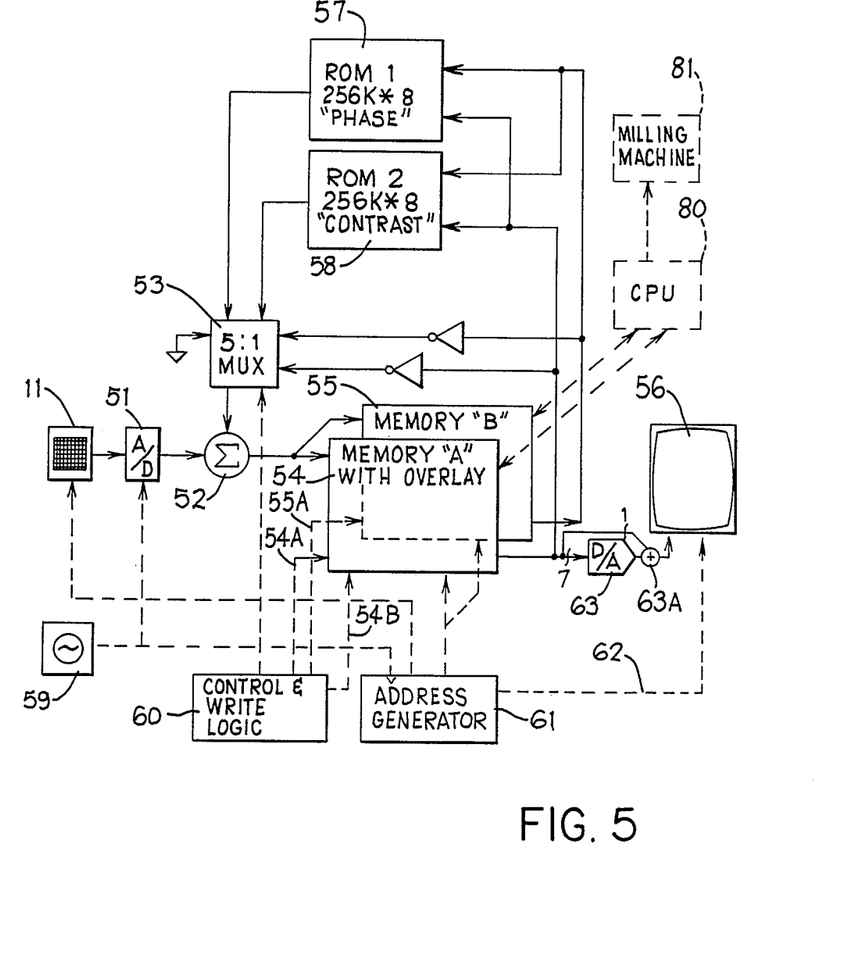
FIG. 5 is a schematic block diagram of a dual bank field store memory and associated hard-wired arithmetic unit which implement the complex data transform in a very efficient fashion.

This latter image, which after the acquisition trigger is almost instantaneously displayed on the monitor 56 in place of the search mode live image, has the desired pseudoplastic character and closely resembles the live image which appeared on the monitor prior to the trigger. The similarity of these images enables the operator to make a rapid judgement of the quality of the record. (If, for instance, the operator's hand shifted or trembled during the acquisition, the resulting image might be blurred and exhibit a "zebra pattern".) If the record is not acceptable, the dentist returns to search mode and starts over. If the dentist accepts the record, he or she can immediately begin the design of the inlay, crown or other indicated restorative work, since all necessary raw data is, at this point, present in memory.

The reconstruction is an interactive graphic procedure, which utilizes the pseudoplastic contrast image as a backdrop upon which all additional data is entered and displayed. Research of the inventors has shown that this technique is much more efficient in intelligibility than any method which utilizes other representations of 3D entities, such as stereoscopic grids. An advantage of the method presented here is the fact that the pure 3D data is complemented by the contrast information, which unveils all the fine detail, edges, fissures, glare spots, etc, namely all features essential for visual interpretation. An example should illustrate the benefit of this technique.

Assume a preparation in a tooth has a section which extends down to the gum level, or in other words has sections where there is no noticeable difference in depth between the preparation and the gum. The machine, assisted by the dentist, has to accurately identify and track the edge of the preparation to ensure perfect marginal adaptation of the restoration. This task is next to impossible if the tracking of the edge must be based on depth information alone.

The memory is organized into two banks, bank A at 54 containing the displayed 2D pseudoplastic image and bank B at 55 storing the 3D depth profile which is in the form of a z-elevation for each x/y point and is normally not displayed. The entire operator interaction takes place based upon the pseudoplastic image in bank A. All the lines drawn in this image are, however, transferred to bank B, and stored in place of corresponding z values therein. The three-dimensional data set defining the restoration is built up as a framework. In order to define the contours of this framework, bank A is equipped with an overlay, which allows storage and display of these lines without affecting the underlying contrast data. Lines or points are entered in a familiar fashion, by steering a cursor with a mouse or trackball. Besides all entries from the operator, results obtained by the reconstruction program are also stored in and displayed from the bank A overlay, where they can be manually edited, if necessary.

The memories 54 and 55 are each a conventional $65K \times 8$ memory. A single write enable line 55A is provided line 55A will cause the 8 bits of data present at the data inputs of the memory 55 to be written into the 8 bits of the word thereof currently being addressed by the address generator 61. In contrast, two separate write enables 54A and 54B are provided for the memory 54. For each word of the memory 54, a pulse on the write enable line 54A causes data to be written into seven bits of the word currently being addressed by the addresss generator 61, whereas a pulse on the write enable line 54B causes data to be written into the remaining bit of the word being addressed. Thus, the $65K \times 8$ memory 54 can conceptually be considered to be two 30 separate memories, namely a $65K \times 7$ memory which stores the two-dimensional pseudoplastic image and a $65K \times 1$ memory which stores the overlay. The second data output of the $65K \times 7$ portion of the memory 54 is connected to the inputs of a digital-to-analog convertor 63, and the analog output of the convertor 63 is connected to one input of an adder 63A, the output of the adder being connected to the display 56. The one-bit data output of the $65K \times 1$ portion of the memory 54 is connected directly to a second input of the adder 63A. A conventional central processing unit 80 can, in a conventional manner, read and write data to and from the memory 55 and each portion of the memory 54. At the beginning of the search mode, a pattern such as a reticle can be written into the $65K \times 1$ overlay portion of the memory. During the search mode, data is written only into the $65K \times 7$ portion of the memory 54. Consequently, as the 8 bit word from the memory 54 is read out for purposes of producing a visually perceptable image on the display 56, 7 bits are applied directly to the inputs of the convertor 63 whereas the 8 (overlay) data is applied directly through input of the adder 63A. If the overlay bit is a "1", it will cause the adder 63A to produce an output which causes the corresponding pixel of the display 56 to have maximum brightness, regardless of the output of the convertor 63. In contrast, if the overlay bit is a "0", the output of the adder 63A and thus the brightness of the corresponding pixel will be directly proportional to the output of the convertor 63. Consequently, the pattern such as a reticle stored in the $65K \times 1$ overlay portion of memory 54 will appear on the display 56 with maximum brightness, the remainder of the image on the display 56 being defined by the data stored in the $65K \times 7$ portion of memory 54.

Figure 4A:
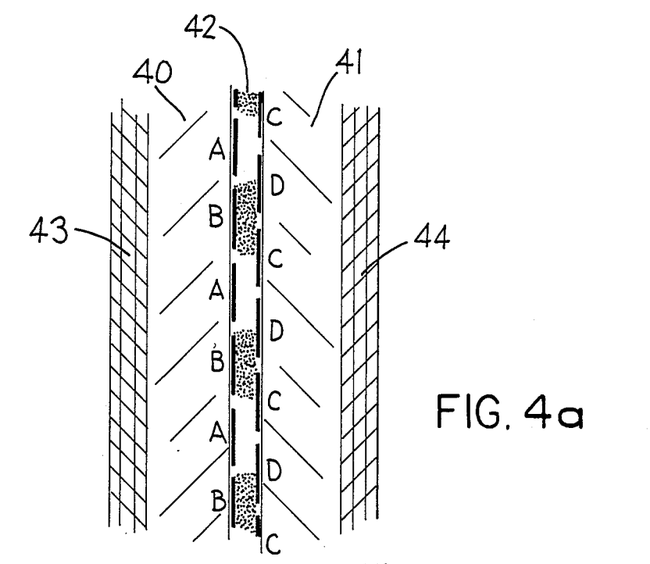

In order to explain the acquisition and transformation principle, attention is drawn to the scan head (FIG. 2). The housing, which has been shaped to meet specific operating conditions, contains the following system components. The light source 2, preferably an infrared LED, radiates light through the condensor 3 and the ruling 4. The ruling 4 is supported by the piezoelectric translator 5, which can displace the ruling perpendicular to the optical axis in increments of 90°. The ruling 5 can be of conventional design (a pattern deposited on glass) and can be moved mechanically. (A more elegant implementation uses, instead of the ruling 4 and translator 5, a liquid crystal cell 40-44 which is shown in FIG. 4a, does not require any moving parts and is described in detail below.) The pattern of the ruling 4 is projected onto the prepared tooth 10 through the lens assembly 8. Essential elements include the double stop aperture 7 and the beam splitter 6, which separate the illuminating light path from the reflected light path, and establish the angle of parallax used for triangulation. The field lens, cemented to the exit end of the elongated prism 9, establishes telecentricity. The solid state image sensor 11 detects the light scattered from the prepared tooth 10 and converts it to a raster-scanned video signal. Terminating and driving circuitry are located on a circuit board 12. The scan head is linked to the signal processing unit by a multi-wire cable 13.

The search mode operation, and the simultaneous generation of the 3D profile and the 2D pseudoplastic contrast image, are now explained, referring to FIGS. 3a-3d. Theoretically, a wide variety of patterns can be used for 3D determination. In the preferred embodiment, a stripe pattern with a 50% duty cycle has been used. The pattern is regular, or in other words has straight, parallel stripes of constant period. Analogous to time dependent signals, one 360° period of the pattern is defined as the spatial interval from one black to white (opaque to transparent) transition to the next identical transition. This 360° period is subdivided into phases, for example a transition of white to black (transparent to opaque) occurs at 180°. If the ruling pattern originally has sharp opaque to transparent and transparent to opaque transitions (thus corresponding in intensity to a square wave along a line perpendicular to its stripes) and is projected onto the tooth and back imaged onto the sensor, a considerable reduction in "sharpness" takes place at the transitions. This effect causes the intensity pattern detected by the sensor to look essentially sinusoidal in a direction perpendicular to the stripes, rather than like a square wave. Let us now observe this pattern throughout the various stages of the search and acquisition mode.

Figure 3A:
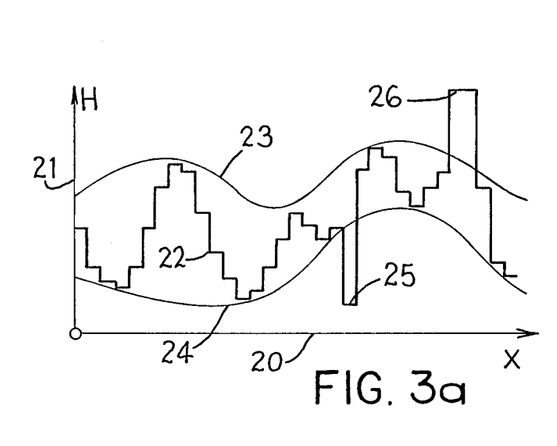
FIG. 3a is an oscillogram of the intensity pattern recorded along a section of a specific sensor line during a first cycle of 3D data acquisition using the sensor of FIG. 2.

Assuming a stationary ruling, an exemplary reading taken along a line on the sensor perpendicular to the pattern stripes will detect the intensity values shown in FIG. 3a. The horizontal axis 20 represents the locations X of the sensor pixels along this line. For each location X a value H is detected, which is proportional to the light intensity scattered back onto the sensor pixel from a corresponding point on the tooth surface. In practice, however, the intensity signal is perturbed by a number of side-effects which all, more or less, tend to degrade the accuracy of the measurement.

The method described in this application involves a way to detect, classify and cancel these interferences. If we interpolate the H-values along a scan line, we obtain the curve 22. This curve is modulated by different factors. We first notice the sinusoidal modulation generated by the ruling pattern. As we know (from U.S. Pat. No. 4,575,805), the phase of this sinusoid contains the depth information. The envelope 23, which spans the positive peaks of the curve 22, shows the intensity modulation, as detected during the search mode. High intensities are detected from areas perpendicular to the line of sight, while walls appear darker. This image of FIG. 3a suggests how the striped ruling pattern (venetian blind pattern) can be cancelled from the live image. Suppression can be accomplished in two ways:

(a) By physically removing the ruling 4. (The liquid crystal cell of FIG. 4a, which is discussed later, facilitates a more elegant implementation of this idea.)

(b) By oscillating the ruling in synchronism with the frame rate. The detector 11 integrates the light sensed for a frame period of 33 msec (the duration of one TV field or screen image). At the end of this frame period, the accumulated charge is transferred to a readout register. If during this 33 msec period the ruling 4 is physically positionally oscillated in a way so as to let equal amounts of light strike each sensor element, the pattern will disappear. The easiest way to achieve this is to "wobble" the ruling in a harmonic fashion (sinusoidal deflection) with an r.m.s, value of half the period of the ruling pattern. This deflection or wobble is effectuated by the piezoelectric element 5.

Besides the upper envelope 23, the lower counterpart envelope 24 must now be discussed. It contains all the unwanted components, mostly stray light (light not backscattered from the tooth) and the dark current of the sensor cells (current which flows even when no illumination falls on the cell). Stray light may also originate from within the scan head or from external light sources; both are clutter components for our purposes. This undesired lower envelope 24 must be cancelled, since it does not contain information pertinent to our 3D acquisition goals. This cancellation is accomplished by subtraction of two image records with patterns 180° out of phase (FIG. 3a)

The difference signal between 23 and 24 can be regarded as the contrast function for the section of the line under investigation.

Special attention is directed toward two typical real-life artifacts, namely blemished and saturated sensor elements. The point 25 indicates a blemished element. Such blemishes, or blind spots, are a result of permanent impurities or misalignments introduced into the sensor 11 during the semiconductor manufacturing process. Single point blemishes, blemish clusters, or even partial blemish columns are not uncommon defects of todays solid-state sensors. Unblemished devices are a prime selection from a given lot of manufactured devices and often are not affordable for commercial equipment. It is thus mandatory that a 3D acquisition system be designed to cope with this problem. The second artifact is illustrated by the point 26, where the sensor is temporarily driven into saturation by excessive glare from the tooth surface. Since such a spot would yield an imperfection on the surface of the machined dental part, it must also be suppressed.

Figure 3B:
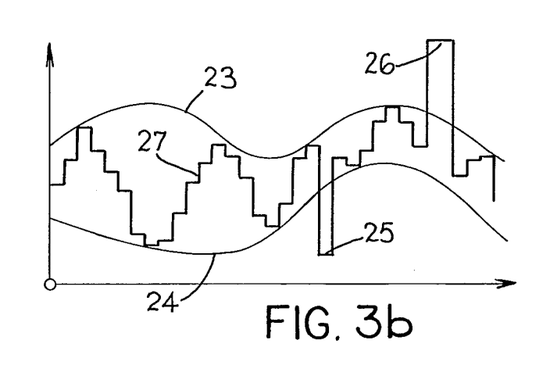
FIG. 3b is an oscillogram similar to FIG. 3a but showing the situation for the same section after a ruling pattern has been spatially shifted by 180° of phase.

Now observe how the acquisition continues. Starting from the situation illustrated in FIG. 3a, the ruling is shifted by 180°. In other words, light intensity peaks in the illumination pattern become valleys and vice versa. (The same portion of the same sensor line is diagrammed, and the light source 2 generates a constant light intensity). The intensity curve 27 has followed this 180° shift whereas, since the same tooth surface is being sensed, both the upper 23 and lower 24 envelopes have remained unchanged. Room light, flickering at 60 cycles, also contributes the same offset in either case). The special cases of a blemish at 25 and glare at 26 have not changed their respective magnitudes either. Subtraction of the waveform given in FIG. 3b from the one in FIG. 3a yields the plot of FIG. 3c. The first thing to be noticed is that the points 25 and 26 both yield a zero difference signal. The sinusoidal curve 28 resembles the original curve 23, but has twice the amplitude. Also note that the signal has become bipolar, in that it oscillates about the zero line. The curve 28, obtained by subtraction, is also defined by an envelope pair, namely the envelope curve 29 for positive peaks and the symmetrical counterpart envelope 30 for negative peaks. Envelope 29, unlike envelope 23 in FIG. 3a, describes the contrast rather than local point intensity. The contrast is defined as the intensity detected at maximum illumination minus the intensity at minimum illumination. (In other words, the intensity due to transparent portions of the ruling minus the intensity due to opaque portions of the ruling, both as reflected from the same point on the tooth.) While the intensity data of the video signal contains a considerable amount of stray light and dark current components, the contrast data contains only the signal relevant for our measurement. If another pair of differential signals, similar to those of FIGS. 3a and 3b, are recorded with the ruling in the 90° position and in the 270° position, respectively, the difference signal is the curve 31 shown in FIG. 3d. Again, envelopes 29 and 30 outline the bipolar signal 31, which exhibits a 90° phase lead with respect to the curve 28 of FIG. 3c. The two signals 28, 31 can be considered a complex pair describing the spatial frequency, as is also taught in U.S. Pat. No. 4,575,805. The term "complex pair" means that each point on one curve and the corresponding point on the other curve can be treated as the real part "Re" and the imaginary part "Im" of a complex vector. The transform:

$$\theta = \arctan \frac{Im}{Re} \text{ (if } Im > 0\text{)}$$

$$\theta = 180° + \arctan \frac{Im}{Re} \text{ (if } Im < 0\text{)}$$

defines the phase of the vector.

The other half of the transform, disregarded so far:

$$C = \sqrt{Re^2 + Im^2}$$

describes the contrast as defined above. In order to rapidly compute $\theta$ and $C$, a hard-wired arithmetic unit, in the form of two ROM's 57 and 58 containing look-up tables, has been incorporated into the image memory shown in FIG. 5.

Two substantial benefits result from this extension:

(a) The contrast image, when displayed, yields the aforementioned pseudoplastic image, which shows all the subtle details indispensable for the visual interpretation of the record.

(b) Each contrast value can be used as a weight attributed to the corresponding individual pixel. Since the inventive system is based on digital data processing, a decrease of the backscattered light intensity results in a coarsely quantized value which, in turn, leads to a correspondingly rough phase determination, in other words, a larger error. Interpolation of neighboring pixels is a common remedy in such situations. Statistical and/or arithmetic filtering can reduce the errors, but sacrifices spatial resolution. If, as in our case, individual pixels can be weighted, the statistical processing becomes much more powerful. Venturing momentarily into the domain of image processing, consider the cases of "blemish" and "glare" discussed above in this regard. As we have seen, the two difference signals 28 and 30 both have a value of zero for these special points. No phase value can be assigned in either case. On the other hand, since the contrast value is also zero, these pixels can be flagged as "don't cares" for the interpolation process. Besides this extreme case, low contrast values can in general be compared against a threshold, and then only pixels having contrasts exceeding a given threshold are used to generate the interplated phase/depth value. While more elaborate schemes can be devised, these two cases clearly exemplify the power of the combined phase and contrast determination and processing.

FIG. 4a is a section through the liquid crystal cell which, as mentioned above, can be stationarily supported in the housing 1 (FIG. 2) of the scan head in place of the ruling 4 and element 5. Between two glass sheets 40 and 41, a space is filled with a liquid 42 in a well-known fashion. Other components, which represent the current state-of-the-art, are polarizers 43 and 44 laminated to outer surfaces of the glass sheets. In the preferred embodiment, the system has been optimized for a wavelength of 850 nm, determined by the emission spectrum of the particular LED 2 selected for use in the scan head. The unique feature of this liquid crystal element is its electrode pattern, which facilitates generation of the desired stripe pattern, and shifting of this pattern in increments of 90° without physical movement of the liquid crystal element. On the left side of the cell, alternate elongate and parallel electrode fingers A and B, and on the right side similar electrode fingers C and D, have been etched on the inner surface of the glass. All A electrodes are connected by a not-illustrated common bus tied to an external contact. Likewise, electrode fingers B, C and D are each connected to a respective bus which is in turn connected to a respective external contact. An important detail is the staggered placement of the left fingers A and B with respect to the right fingers C and D. The four electrodes A, B, C and D are excited by square waves, examples of which are shown in FIG. 4B at 45 and 46, in order to generate the desired four-phase ruling pattern by electronic means.

Figure 4B:
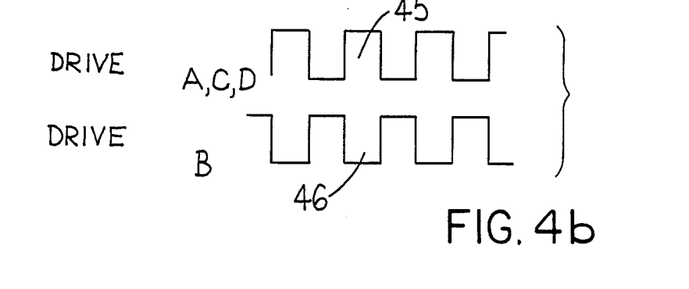

In FIGS. 4a and 4b, the B electrode fingers are driven by signal 46, and electrode fingers A, C and D are driven by the signal 45. Wherever opposing electrodes are driven by complimentary signals, the crystals are aligned and the light through the cell is blocked by the crossed polarizers. The dotted areas in 42 diagrammatically illustrate this phenomenon. The manner in which the signals 45 and 46 are applied is varied in a cyclic manner so that signal 46 is successively applied to each of the electrodes A–D while the signal 45 is applied to the remaining three electrodes. This cyclic permutation of the drive signals moves the pattern in 90° increments with an accuracy unachieved by the mechanically moved ruling at 4 and 5 in FIG. 2. The other advantage of the liquid crystal cell with respect to the mechanically moved ruling occurs in the search mode, during which the ruling can be turned off (so that there are no opaque regions at all) simply by applying equal voltages to all four electrodes A–D.

The memory and arithmetic unit used in the image memory of the computer in the preferred embodiment are illustrated in FIG. 5. External signals and control paths have been omitted or shown diagrammatically in broken lines for clarity. These signals manage the general timing and the communication to the central processing unit, which can access each individual pixel in memory bank 54 or memory bank 55 by performing either a read or write cycle. The memory system is designed to implement the following modes:

A. Search mode or acquisition of an image, wherein data received from scan head sensor 11 through an A/D converter 51 is written directly into one of the memory banks.

B. Read-modify-write mode, wherein the contents stored in a specific memory bank are subtracted from the incoming digitized data, and the difference written back into that bank, on a word by word basis.

C. Transform mode, where pairs of data, stored in corresponding words of banks 54 and 55, are converted from the cartesian coordinate (Re, Im) representation to phase/contrast pairs.

During the search mode, the ruling is wobbled synchronously or is turned off, and the signal from the image sensor 11 is digitized by the A/D converter 51 and enters one input port of the adder 52. The other adder input port is tied to the output of a multiplexer 53. During search mode, the multiplexer 53 selects a zero input, designated in FIG. 5 by a ground symbol. The incoming signal from converter 51 thus passes through the adder 52 unchanged, and is written into the memory bank 54 by means of the control and write logic 60 and the address generator 61. The address generator 61 is responsible for the horizontal and vertical (row and column) addresses which select different memory locations. The image sensor 11 is addressed likewise. The sensor 11 is continuously read, the digitized data stream written into the memory 54, and the output of memory 54 converted back to analog by D/A converter 63 and displayed on the monitor 56 as a live image. The sync signal 62 for the monitor 56 is supplied by the address generator 61. Memory bank 54 has an overlay plane with a separate write line, permitting reticles or other sighting aids to be superimposed on the search mode image, as discussed above. Not only can general purpose markers, such as a millimeter grid, be written into the overlay, but a more interesting capability becomes possible: contours taken from a previous record or from a tooth "library" can be superimposed on the live image. This feature allows alignment of consecutive records in 3D space. If, for example, a tooth has to be restored by adding a crown, the dentist may wish to take a first record of the stump preparation, outline of the tooth under reconstruction and adjacent portions of its neighbors. A second record, mapping a wax build-up in which the patient has "carved" the path that opposing teeth generate on the biting plane, is then taken. The outline of the first record is used to align the second record with the first record. This alignment can be visually accomplished easily by the dentist, namely by visually observing the display screen while manually adjusting the position of the scan head until superposed displays of the first record and the live image are aligned, at which time the second record is recorded. To achieve the same result solely by computer is a highly difficult undertaking. The overlay feature can also be used the other way around, by recording the tooth surface with an old filling still in place. Contours are then traced by the dentist. Once the old filling and decayed tooth substance has been removed, the second record can be taken, again by first properly aligning the scan head to align the superimposed images. Another similar situation arises in the case where the dentist chooses to cover a badly discolored and/or demineralized incisor (front tooth) with a thin veneer. In this setting, it is again useful to take a record before the preparation, to take a second image with a thin slice of material removed, and to "fuse" the two records.

Figure 3C:
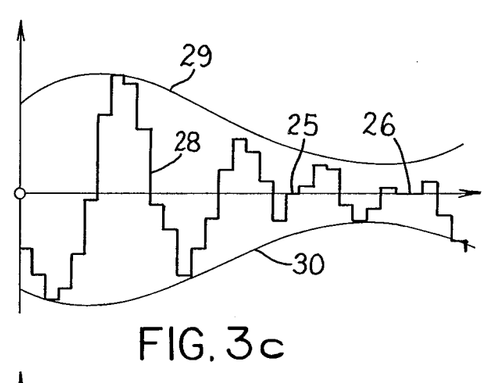
FIG. 3c is an oscillogram showing the difference between the oscillograms illustrated in FIGS. 3a and 3b.
Figure 3D:
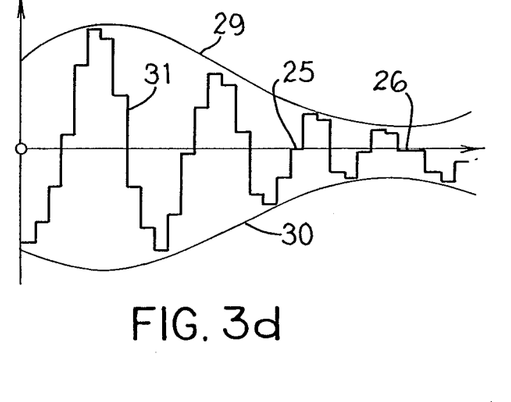
FIG. 3d which is an oscillogram similar to FIG. 3c shows a similar difference, namely between two not-illustrated signals which lead the ones shown in FIGS. 3a and 3b in phase.

The dentist can, at any instant during the search mode, initiate or trigger the actual 3D acquisition. If this trigger occurs, the following steps take place in rapid sequence. The ruling is set to its 0° position. During one TV frame or screen the digitized intensity data (curve 22 in FIG. 3a) is written into bank 54. For the next TV frame, the ruling is advanced to its 90° position, and an intensity pattern shifted by 90° is written into bank 55. The multiplexer 53 selects the zero input for the other adder input port for both the 0° and the 90° position. For the third frame the feedback loop is opened, so that the inverted output of bank 54 is added to the −180° signal "on the fly". The resulting difference signal 28 of FIG. 3c is thus written into bank 54 in place of the original data. This operation is commonly known as read-modify-write. For the last frame of the sequence, the ruling is advanced to the 270° position and a similar read-modify-write operation on the bank 55 stores therein the other difference signal (31 of FIG. 3d).

The recording session is now terminated, and the scan head and the A/D converter 51 are turned off (so that the output becomes zero). The transform is now initiated. The address generator successively scans all pixels by simultaneously addressing locations in bank 54 and bank 55. This scanning retrieves complex pairs from the two banks. At any given time a respective such pair is being applied to both of the read only memories (ROMS) 57 and 58. These two look-up-tables have been programmed to contain the $\theta$ and C values which would result from the equations discussed above. Each located contrast value C is written back into the respective pixel location of bank 54 just before the address generator 61 addresses the next pixel location. The same read-modify-write operation is also performed in bank 55, where the phase values $\theta$ are stored. By this hard-wired architecture, a high speed of transformation can be achieved. In particular, 65,000 data pairs can be transformed in approximately 150 ms, which means the live image is replaced by an image based on the recorded and processed data almost before the dentist can blink.

The method described in this application combines (1) a way to accurately orient a scan head with respect to a tooth to be reconstructed with (2) a technique to display the three-dimensional result of the record in a highly intelligible fashion with virtually no delay.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A method of facilitating acquisition of data defining the three-dimensional shaped of prepared teeth and their immediate vicinity, comprising the steps of: displaying on a video display a live image from a scan head, manually orienting the scan head relative to the prepared teeth while observing the image of the teeth on said video display, thereafter generating from data produced by said scan head in a selected orientation corresponding depth and contrast images, and thereafter processing said depth image based on said contrast image.

2. A method according to claim 1, including the step of superimposing graphic markers on said image displayed on said video display to facilitate an on-line alignment of the teeth displayed in said live image with reference data from previous data acquisitions.

3. A method according to claim 1, wherein said processing step includes the additional step of utilizing data from said contrast image to weight data in said depth image.

4. A method according to claim 1, including the additional steps of: displaying said contrast image on said video display as a pseudoplastic image, adding two-dimensional contour lines to said pseudoplastic image, and generating from said two-dimensional contour lines in said pseudoplastic image three-dimensional contour lines for said depth image based on said correspondence of said depth and contrast images.

5. An apparatus, comprising manually positionable scan head means for utilizing active triangulation to generate data representing a running sequence of images of a prepared tooth and its immediate neighborhood, means operable during a search mode when said scan head means is being manually positioned for cancelling from said data artifacts generated by said triangulation so each of said images in said sequence is an uncluttered high resolution image, and means operable during an acquisition mode immediately following said search mode for acquiring and storing a subset of said data corresponding to a selected said image of said sequence occurring at a given point in time.

6. An apparatus as set forth in claim 5, including data processing means for generating from said data subset after said given point in time a contrast image, and video image display means for providing a visual display of said contrast image.

7. An apparatus according to claim 5, comprising arithmetic means for generating from said subset of data a pair of images defined with respect to a common two-dimensional coordinate system, namely a contrast image and a congruent three-dimensional depth image which contains for each point in said two-dimensional coordinate system a depth value representing a displacement in a third dimension.

8. An apparatus according to claim 7, wherein said scan means includes a ruling which casts a striped pattern of light from a light source onto the prepared tooth through a lens assembly, means responsive to backscattered light from the tooth for producing an image of the prepared tooth on a photosensor, and means for effecting phase shifts of said striped light pattern; and wherein said subset of data includes a sequence of said high resolutions images which are each recorded at a different phase of the striped light pattern.

9. Apparatus according to claim 8, wherein said ruling is a liquid crystal cell which is transparent prior to said given point in time and which has spaced opaque stripes during acquisition of said subset of data.

10. Apparatus according to claim 9, wherein said liquid crystal cell has electrodes arranged to allow the ruling pattern to be selectively shifted in increments of a fraction of the distance between two adjacent said stripes of said pattern.

11. Apparatus according to claim 8, wherein said means for cancelling artifacts includes means for wobbling said ruling in a manner synchronized to a frame rate.

12. An apparatus according to claim 7, comprising: means for entering and storing graphic information and for superimposing said graphic information on one of said contrast and depth images.

13. In a method for noncontact topographic scanning of a three-dimensional contour on an object, including the steps of: directing a predetermined intensity pattern of light onto the contour so that a corresponding intensity pattern of light will be backscattered therefrom, the varying intensity pattern of said backscattered light being a measure of the three-dimensional contour on the object; directing said pattern of said backscattered light onto electro-optical light sensing means; periodically reading from said light sensor means electrical data representative of the image directed onto said sensor and displaying said electrical data on a video display; thereafter successively moving said intensity pattern relative to the object to at least two different positions and reading from said light sensor means for each said position of said pattern a respective set of electrical data, and storing each said set of electrical data; and calculating from said stored sets of electrical data a digital three-dimensional image of the contour; the improvement comprising the step of calculating from said stored sets of electrical data a digital two-dimensional contrast image of the contour and the step of continuously displaying on said video display said two-dimensional contrast image, said contrast image being for each point on the contour the difference between the respective backscattered light intensities detected by said light sensing means for illumination of said point with maximum and minimum light intensities of said pattern.

14. The method of claim 13, including during said step of periodically reading electrical data from said sensor and displaying it on said video display, the step of superimposing on the images being displayed on said video display a further image.

15. The method of claim 13, including the step of adding two-dimensional contour lines to said two-dimensional contrast image, and thereafter converting said two-dimensional contour lines to three-dimensional contour lines and incorporating said three-dimensional contour lines into said three-dimensional image of the contour.

16. The method of claim 13, including the step of weighting each data element in said three-dimensional image of said contour in dependence on the value of a corresponding data element of said contrast image.

17. The method of claim 13, wherein said step of moving said intensity pattern includes the step of positioning said intensity pattern at first, second, third and fourth positions in which said pattern has respective relative phase offsets of 0°, 90°, 180° and 270° with respect to a period of said pattern, wherein said storing step includes the step of storing first, second, third and fourth said sets of electrical data which respectively correspond to said first, second, third and fourth positions of said pattern, and wherein said step of calculating said contrast image includes the steps of subtracting said third data set from said first data set to yield a fifth data set, subtracting said fourth data set from said second data set to yield a sixth data set, and carrying out a rectangular to polar conversion for each of a plurality of pairs of elements from said fifth and sixth data sets to obtain a polar angle and polar magnitude, said polar magnitudes being a data set which is said contrast image.

18. In an apparatus for noncontact topographic scanning of a three-dimensional contour on an object, including means for directing a predetermined intensity pattern of light onto the contour so that a corresponding intensity pattern of light will be backscattered therefrom, the varying intensity pattern of said backscattered light being a measure of the three-dimensional contour on the object; means for directing said pattern of said backscattered light onto electro-optical light sensing means; means for periodically reading from said light sensing means electrical data representative of the image directed onto said light sensing means; means for displaying said electrical data on a video display; means for thereafter successively moving said intensity pattern relative to the object to at least two different positions, for reading from said light sensor means for each said position of said pattern a respective set of electrical data, and for storing each said set of electrical data; and calculating means for calculating from said stored sets of electrical data a digital three-dimensional image of the contour; the improvement comprising wherein said calculating means includes means for calculating from said stored sets of electrical data a digital two-dimensional contrast image of the contour, and including means for thereafter continuously displaying on said video display said two-dimensional contrast image, said contrast image being for each point on the contour the difference between the respective backscattered light intensities detected by said light sensing means for illumination of said point with maximum and minimum light intensities of said pattern.

19. The apparatus of claim 18, wherein said means for storing said electrical data includes first and second memory banks which each have a data input and a data output, and wherein said calculating means includes: first and second read only memories which each have two address inputs respectively connected to said data outputs of said first and second memory banks and which each have a data output, said first read only memory producing at its data output a polar coordinate angle corresponding to two data values supplied to its respective address inputs and representing a pair of rectangular coordinates, and said second read only memory producing at its data output a polar coordinate magnitude corresponding to two data values supplied to its respective address inputs and representing a pair of rectangular coordinates; an adder having a first input connected to an output of said means for periodically reading, having a second input, and having an output connected to said data input of each said memory bank; and means for selectively supplying to said second input of said adder one of: said data output of said first read only memory, said data output of said second read only memory, a value which is the complement of said data output of said memory bank, a value which is the complement of said data output of said second memory bank, and a value of zero.

20. The apparatus of claim 19, wherein said means for displaying includes a digital to analog converter having an input coupled to said data output of one of said first and second memory banks and having an output coupled to an input of said video display.

21. The apparatus of claim 20, including an overlay memory having a data output; and a further adder having a first input connected to said output of said analog to digital converter, having a second input connected to said data output of said overlay memory, and having an output connected to said input of said video display.

22. In an apparatus for noncontact topographic scanning of a three-dimensional contour on an object, including: light source means for generating light and means for directing light from said light source means onto the contour; pattern generating means disposed in the path of the light from said light source for imparting to said light a predefined pattern of intensity; light sensor mans at a predetermined location; and means for directing light backscattered from said contour onto said light sensing means; the improvement comprising wherein said pattern generating means includes a liquid crystal cell having therein a liquid crystal material through which light traveling from said light source means to said object passes, said liquid crystal cell having electrode means responsive to electric stimulation for generating transparent regions and opaque regions in said liquid crystal material in the form of said predefined pattern.

23. The apparatus of claim 22, wherein in the absence of said electrical stimulation of said electrode means said liquid crystal material of said liquid crystal cell is transparent to light from said light source means.

24. The apparatus of claim 23, wherein said predefined intensity pattern is a plurality of parallel stripes, wherein said electrode means includes first, second, third and fourth groups of electrode fingers which are all parallel, said fingers of said first and second groups being arranged in a uniformly spaced, alternating manner on a first side of said liquid crystal material and said fingers of said third and fourth groups being arranged in a uniformly spaced, alternating manner on a second side of said liquid crystal material opposite from said first side so that, in a direction substantially perpendicular to said stripes and said path of light travel, each of said fingers of said third and fourth groups is aligned with a respective space between and has edge portions which each overlap an edge portion of a respective one of two respective adjacent said fingers on said first side of said liquid crystal material.

25. The apparatus of claim 24, including means for applying a first square wave signal to all of the electrode fingers in a selected one of said groups and for applying a second square wave signal which is an inverse of said first square wave signal to all of the electrode fingers in each group other than said selected group.

26. The apparatus of claim 25, including means for successively causing each of said groups to be said selected group according to a predetermined sequence.

27. In an apparatus for noncontact topographic scanning of a three-dimensional contour on an object, including: light source means for generating light and means for directing light from said light source means onto the contour; pattern generating means disposed in the path of light from said light source means for imparting to said light a predefined intensity pattern; electro-optical light sensor means at a predetermined location and means for periodically reading from said sensor means at a frame rate respective sets of electrical data which each represent a respective image of light intensity impinging on said sensor means; and means for directing light reflected from the contour onto said light sensing means; the improvement comprising wherein said pattern generating means includes means for selectively effecting oscillatory movement of said intensity pattern in a direction substantially perpendicular to a path of travel of light through said pattern generating means, said oscillatory movement being effected at a frequency which is an integer multiple of said frame rate of said sensor means.

28. The apparatus of claim 27, wherein said intensity pattern includes a plurality of parallel stripes of high light intensity separated by stripes of low light intensity, said light intensity stripes of high and low intensity having uniform widths and extending substantially perpendicular to said direction of oscillatory movement, said oscillatory movement having an amplitude which is approximately equal to the width of one of said stripes.

* * * * *

UNITED STATES PATENT AND TRADEMARK OFFICE
CERTIFICATE OF CORRECTION

PATENT NO. : 4 837 732
DATED : June 6, 1989
INVENTOR(S) : Marco BRANDESTINI et al It is certified that error appears in the above-identified patent and that said Letters Patent is hereby corrected as shown below:

Column 14, line 62; delete "of" (first occurrence).

Column 14, line 63; change "shaped" to ---shape---.

Column 15, line 56; change "resolutions" to ---resolution---.

Column 16, line 5; change "superimposing" to ---superposing---.

Column 18, line 10; change "mans" to ---means---.

Column 18, line 47; after "each" insert ---said---.

Signed and Sealed this

Twentieth Day of February, 1990

*Attest:*

JEFFREY M. SAMUELS

*Attesting Officer*   *Acting Commissioner of Patents and Trademarks*